United States Patent [19]

Tamabayashi et al.

[11] 4,110,366

[45] Aug. 29, 1978

[54] PROCESS FOR PRODUCING ALKALI METAL STYRENESULFONATE

[75] Inventors: Hanzo Tamabayashi; Tatsuo Hattori; Tetsuo Tanaka; Yasuhiro Oda; Keiichi Kihara, all of Shin-nanyo, Japan

[73] Assignee: Toyo Soda Manufacturing Co., Ltd., Japan

[21] Appl. No.: 746,531

[22] Filed: Dec. 1, 1976

[30] Foreign Application Priority Data

Dec. 17, 1975 [JP] Japan ................................. 50-149539

[51] Int. Cl.$^2$ ............................................. C07C 143/24
[52] U.S. Cl. ............................. 260/505 N; 260/501.21
[58] Field of Search ..................................... 260/505 N

[56] References Cited

U.S. PATENT DOCUMENTS 2,451,549  10/1948  Gzemski ........................ 260/505 N Primary Examiner—A. Siegel
Attorney, Agent, or Firm—Oblon, Fisher, Spivak, McClelland & Maier

[57] ABSTRACT

An alkali metal styrenesulfonate is produced by extracting from an aqueous solution by contacting an aqueous solution containing an alkali metal halide and an alkali metal styrenesulfonate with an organic solvent containing a protonic acid salt of an amine of more than 7 carbon atoms as the extracting reagent, and then back-extracting the styrenesulfonic acid anions with an aqueous solution of an alkali metal hydroxide.

5 Claims, No Drawings

PROCESS FOR PRODUCING ALKALI METAL STYRENESULFONATE

BACKGROUND OF THE INVENTION

1. Field of the Invention

The present invention relates to a process for producing an alkali metal styrenesulfonate by extracting from an aqueous solution containing an alkali metal halide and an alkali metal styrenesulfonate, and back-extracting styrenesulfonic acid anions.

2. Description of the Prior Art

In the past, styrenesulfonates have been produced by sulfonating a halogenoethylbenzene with chlorosulfonic acid or sulfur trioxide and reacting the resulting halogenoethylbenzenesulfonyl chloride or halogenoethylbenzenesulfonic acid with an alkali metal hydroxide in water to dehydrohalogenate the sulfonic acid or sulfonyl chloride to the product styrenesulfonate as shown by the reaction formulae (1) and (2). After the reactions the product is obtained by crystallizing the crude product and then filtration.

Reaction formula (1):

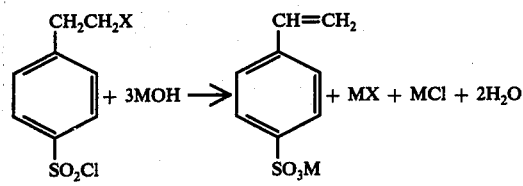

Reaction formula (2):

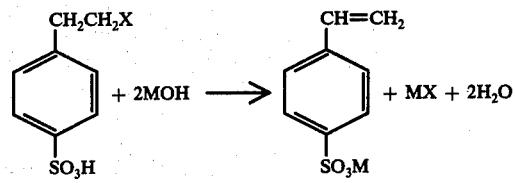

wherein M represents an alkali metal such as K, Na or Li and X represents a halogen such as Cl or Br.

However, the conventional process has various technical problems. For example, the desired alkali metal styrenesulfonate product is highly soluble in water, and consequently it is necessary to minimize the quantity of water used as a solvent. On the other hand, if the quantity of water used is too small, stirring of the reaction mixture containing precipitated material is difficult. The reaction can be effectively conducted at temperatures higher than 100° C to improve crystallization of the product. However, if the temperature is too high, control of the reaction is difficult under the boiling conditions, and the type of reactor material is limited so that it can withstand the aqueous caustic alkali solution at high temperatures.

A need, therefore, continues to exist for a method of preparing styrenesulfonates which overcomes the problems of the prior art procedures.

SUMMARY OF THE INVENTION

Accordingly, one object of the present invention is to provide a process for producing styrenesulfonates of high purity with ease of operation.

Briefly, this and other objects of the present invention as hereinafter will become more readily apparent can be attained in a method of producing styrenesulfonates by preferentially extracting from an aqueous solution containing an alkali metal halide and an alkali metal styrenesulfonate with an organic solvent containing a protonic acid salt of an amine of more than 7 carbon atoms and back-extracting styrenesulfonic acid anions with an aqueous solution of an alkali metal hydroxide.

DETAILED DESCRIPTION OF THE PREFERRED EMBODIMENTS

The discovery upon which the present invention is based is the finding that styrenesulfonic acid anions can be preferentially extracted in the presence of halogen ions and styrenesulfonic acid anions in a solution. In the process of the present invention, the amine which is used to form the protonic acid amine salt extractant is one which contains more than 7 carbon atoms, is an ion-exchange liquid, and is a primary, secondary or tertiary amine containing an alkyl alkenyl, aryl or aralkyl group. Suitable amines which can be employed include: 2-ethylhexylamine, octylamine, decylamine, laurylamine, coconut amine, myristylamine, oleylamine, coconutalkylamine, di-2-ethylhexylamine, tri-2-ethylhexylamine, dimethyloctylamine, dimethyldecylamine, dimethyllaurylamine, dimethylcoconut amine, dimethylmyristylamine, hexadecyldimethylamine, methyldilaurylamine, dimethylstearylamine, tricaprylamine, coconutalkyldimethylamine, toluidine, xylidine, trimethylaniline, ethylaniline, propylaniline, naphthylamine, N-methyltoluidine, N-methylaniline, N-ethylaniline, diphenylamine, N-phenyltolylamine, ditolylamine, N,N-dimethyl toluidine, N,N-diethylaniline, N-methyldiphenylamine,

| | |
|---|---|
| Amberlite LA-1 | <N-dodecenyl(triC$_{12-15}$alkylmethyl)amine> |
| Amberlite LA-2 | <N-lauryl(triC$_{12-15}$alkylmethyl)amine> |
| Primene JMT | <Trialkylmeythylamine having 18 to 24 carbon atoms: (Tradename of Rhom & Haas Co. Ltd.) |
| Primene 81-R | $H_2N-C\genfrac{}{}{0pt}{}{R_1}{R_3}-R_2$ ( $R_1, R_2, R_3$ = alkyl group, total carbon atoms of about 13 ) |
| Amine S-24: | Bis(1-isobutyl-3,5-dimethyl hexyl)amine |
| Amine 21F81: | <1-(3-Ethylpentyl)-4-ethyloctylamine> (Tradename of U.C.C.) |
| Trifathy acid RC-3749: | <N$+$(CH$_2$)$_n$CH$_3$]$_3$ mixture of n-octyl and n-dodecyl > |
| Alamine 336: | <NR$_3$ : R = alkyl group having carbon atoms of 8 to 10> (Tradename of General Mills Co.) | and di(tridecyl)amine, N-benzyl heptadecyl amine, triisooctylamine, and the like.

However, the above amines are by no means the only amines which can be used in the present process since the type of amine used is not critical. Suitable protonic acids which can be used in the preparation of the extractant include hydrobromic acid, hydrochloric acid, sulfuric acid and the like.

Suitable organic solvents used in the present process preferably include those containing as the main component a hydrocarbon of more than 5 carbon atoms such as n-heptane, kerosene, ligroin, and the like; a ketone of more than 4 carbon atoms such as diethyl ketone, di-n-propyl ketone; and an ether of more than 4 carbon atoms such as isopropyl ether, n-butyl ether and the like; an alcohol of more than 4 carbon atoms such as n-butanol, n-amylalcohol and the like.

The ratio of the protonic acid salt of the amine to the organic solvent is preferably 5 to 40 weight percent of the protonic acid salt of the amine to the total mixture.

The concentration of the alkali metal styrenesulfonate in the solution to be extracted in the invention is in a range of 2 weight percent as styrenesulfonic acid anions to the limit of solubility of the styrenesulfonate. There is no limit to the concentration of styrenesulfonate. However, if the concentration is low, a larger volume of the aqueous solution is required to treat the same amount of styrenesulfonic acids anions which is uneconomical.

In the extraction, it is preferable to use the styrenesulfonic acid anions in equivalent or in excess to the ion-exchange capacity of the protonic acid salt of the amine. When the amount of the styrenesulfonic acid anions is less than equivalent, the purity of the product obtained by the following back-extraction is lowered. However, in the case of multi-stage extraction system, it is possible to be less than equivalent, for example, at the first stage. In the back-extraction of the styrenesulfonic acid anions from the extract, an aqueous solution of an alkali metal hydroxide such as sodium hydroxide, potassium hydroxide or lithium hydroxide which corresponds to the alkali metal of the desired styrenesulfonate product is used.

When a product having high purity which does not substantially contain an alkali metal hydroxide is produced, the amount of an alkali metal hydroxide is preferably equivalent or less than equivalent to the amount of the protonic acid salt of the amine. This is not fundamental requirement. In the case of muli-stage extraction system, it is possible to be more than equivalent, for example, at the first stage.

The concentration of the alkali metal hydroxide is preferably controlled so that the concentration of the alkali metal styrenesulfonate in the aqueous solution is less than the solubility limit thereof. The resulting aqueous solution of the alkali metal styrenesulfonate can be used with or without concentration or crystallization.

Having generally described the invention, a more complete understanding can be obtained by reference to certain specific charged which are included for purposes of illustration only and are not intended to be limiting unless otherwise specified.

EXAMPLE 1

Into a 3 liter flask equipped with a reflux condenser and an electromagnetic stirrer were charger 135 g (476 millimole) of bromoethylbenzenesulfonyl chloride and 2240 g of a 4 weight percent aqueous solution of potassium hydroxide (1600 millimole). The solution was stirred at 40° C for 3 hours and then at 55° C for 3 hours in a water bath to control the temperature and to conduct the reaction. The reaction mixture was cooled and adjusted to a pH of 7.0 with hydrochloric acid whereby 2400 g of an aqueous solution containing 427 millimoles of styrenesulfonic acid anions was obtained.

A 370 g amount of the aqueous solution (66 millimoles of styrenesulfonic acid anions) was mixed with 240 g of a 10% ligroin solution of Amberlite LA-1 [N-dodecenyl (tri $C_{12-15}$ alkylmethyl) amine] hydrochloride (ion-exchange capacity: 60 millimoles) with shaking in a separatory funnel for 15 minutes to extract the styrenesulfonic acid anions. After separation of the aqueous phase, the upper phase (ligroin phase) remained and 77.9 g of an aqueous solution of a 4.0 weight percent aqueous solution of potassium hydroxide (56 millimoles) was mixed and shaken with the ligroin phase to back-extract the same whereby 55 millimoles of styrenesulfonic acid anions were recovered as well as 0.8 millimoles of halogen ions (derived from potassium chloride and potassium bromide).

The amount of styrenesulfonic acid anions was determined by quantitative analysis of the double bonds in the styrene sulfonate anions by the bromate-bromide method.

The amount of halogen ions was measured by the Volhard method.

EXAMPLE 2

In accordance with the process of Example 1, the extraction and the back-extraction steps were conducted except that 58.0 g of a 4.0 weight percent aqueous solution of sodium hydroxide (58 millimoles) was used instead of an aqueous solution of potassium hydroxide. Consequently, in the separated aqueous phase, 57 millimoles of styrenesulfonic acid anions were recovered and only 0.4 millimole of halogen ions and 0.7 millimole of potassium were present.

The amount of potassium was measured by the atomic absorption spectroscopy.

EXAMPLE 3

A 30.0 g (113 m mole) of 2-bromoethylbenzenesulfonic acid and 238 g (238 m mole) of 4% aqueous solution of sodium hydroxide were mixed to react them at 60° C for 3 hours. The reaction mixture was cooled and adjusted to a pH of 7.0 with hydrobromic acid whereby 275 g of an aqueous solution containing 104 millimoles of styrenesulfonic acid anions was obtained.

The extraction was carried out by contacting the reaction mixture with 300 g of n-amyl alcohol containing 14.5 g (101 m mole) of p-toluidine hydrochloride and then, the back-extraction was carried out by contacting the organic solution with 196 g (98 m mole) of 2% aqueous solution of sodium hydroxide. Consequently, in the separated aqueous phase, 94 m mole of styrenesulfonic acid anions were recovered and only 0.9 m mole of halogen ions were present.

Having now fully described this invention, it will be apparent to one of ordinary skill in the art that many changes and modifications can be made thereto without departing from the spirit or scope of the invention as set forth herein.

What is claimed as new and intended to be secured by Letters Patent is:

1. A process for producing an alkali metal styrenesulfonate, which comprises:
preferentially extracting styrenesulfonate acid anions from an aqueous solution containing an alkali metal halide and an alkali metal styrenesulfonate in a concentration of 2 wt% to the limit of solubility of the styrenesulfonate with an organic solvent containing a protonic acid salt of an inorganic acid and an amine having more than 7 carbon atoms, which is an ion-exchange liquid and which contains an alkyl, alkenyl, aryl or aralkyl group, wherein the salt is present in an amount of 5–40% to total mixture, as an extracting reagent; and then back extracting styrenesulfonic acid anions with an aqueous solution of an alkali metal hydroxide.

2. The process of claim 1, wherein the amine is a primary, secondary or tertiary amine.

3. The process of claim 1, wherein the organic solvent is a hydrocarbon of more than 5 carbon atoms, a ketone of more than 4 carbon atoms or an ether of more than 4 carbon atoms or an alcohol of more than 4 carbon atoms.

4. The process of claim 1, wherein the protonic acid salt is a hydrochloride, a hydrosulfate, hydrobisulfate or a hydrobromide.

5. The process of claim 1, wherein said alkali-metal hydroxide is sodium hydroxide, potassium hydroxide or lithium hydroxide.

* * * * *